United States Patent [19]

Odorisio et al.

[11] Patent Number: 5,162,408

[45] Date of Patent: Nov. 10, 1992

[54] N-ALKENYL SUBSTITUTED AMINE-N-OXIDE STABILIZERS

[75] Inventors: Paul Odorisio, Edgewater, N.J.; Joseph E. Babiarz, Amawalk, N.Y.

[73] Assignee: Ciba-Geigy Corporation, Ardsley, N.Y.

[21] Appl. No.: 766,497

[22] Filed: Sep. 26, 1991

Related U.S. Application Data

[62] Division of Ser. No. 515,013, Apr. 24, 1990, Pat. No. 5,081,300.

[51] Int. Cl.$^5$ .............................................. C08L 23/36
[52] U.S. Cl. .................................... 524/236; 524/238; 524/241; 524/247; 564/297; 564/299; 252/51.5 A
[58] Field of Search ............... 564/297, 299; 524/236, 524/238, 241, 247

[56] References Cited

U.S. PATENT DOCUMENTS

| | | | |
|---|---|---|---|
| 3,532,762 | 10/1970 | Corbier et al. | 260/677 |
| 4,029,658 | 6/1977 | Samour | 546/341 |
| 4,666,962 | 5/1987 | Ravichandran et al. | 524/99 |
| 4,696,964 | 9/1987 | Ravichandran et al. | 564/300 |
| 4,757,102 | 7/1988 | Ravichandran et al. | 524/95 |
| 4,876,300 | 10/1989 | Seltzer et al. | 524/100 |

*Primary Examiner*—Glennon H. Hollrah
*Assistant Examiner*—Shailendra Kumar
*Attorney, Agent, or Firm*—Luther A. R. Hall

[57] ABSTRACT

N-Alkenyl substituted hydroxylamines of formula I

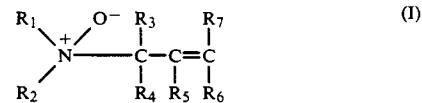

where $R_1$ and $R_2$ are independently hydrogen, alkyl, aryl or phenylalkyl, and $R_3$ to $R_7$ are independently hydrogen, alkyl or substituted alkyl are very effective process stabilizers for polymeric systems providing melt flow stabilization and resistance to discoloration during processing at elevated temperatures as well as effective stabilizers for lubricant compositions.

6 Claims, No Drawings

N-ALKENYL SUBSTITUTED AMINE-N-OXIDE STABILIZERS

This is a divisional of application Ser. No. 515,013, filed on Apr. 24, 1990, now U.S. Pat. No. 5,081,300, issued on Jan. 14, 1992.

This invention pertains to N-alkenyl substituted amine-N-oxide compounds found to be very effective process stabilizers for polymeric systems, especially those processed at elevated temperatures, as well as for lubricant compositions.

BACKGROUND OF THE INVENTION

Organic polymeric materials such as plastics and resins are subject to thermal, oxidative and/or photo-degradation. A great variety of stabilizers are known in the art for stabilizing a diversity of substrates. Their effectiveness varies depending upon the causes of degradation and the substrate to be stabilized. In general, it is difficult to predict which stabilizers will be most effective and most economical for any one area of stabilization. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Saturated tertiary amine N-oxides are known as non-ionic surfactants. The oxidation and rearrangement of selected N-alkenyl(allyl) tertiary amine N-oxides to the corresponding O-alkenyl(allyl) hydroxylamines are taught by A. C. Cope et al., J. Am. Chem. Soc., 71, 3423 (1949); R. F. Kleinschmidt and A. C. Cope, J. Am. Chem. Soc., 66, 1929 (1944); S. Inoue et al., Chem. Letters, 1986, 2035; and Y. Inouye et al., J. Org. Chem. 41, 300 (1976). The use of N-alkenyl-N-oxides of tertiary amines as stabilizers for organic substrates is not taught in the prior art.

OBJECTS OF THE INVENTION

One object of the instant invention is to provide a stabilized composition of (a) an organic material subject to oxidative, thermal or actinic-induced degradation, and (b) an N-alkenyl substituted amine-N-oxide as a stabilizer.

Another object of this invention is to provide selected N-alkenyl substituted amine-N-oxide compounds having efficacious process stabilization properties not possessed by the O-substituted hydroxylamines of the prior art.

Still another object of this invention is to provide lubricating oil compositions stabilized against oxidation, sludge formation and viscosity increases by the presence of the N-alkenyl substituted amine-N-oxide compounds of this invention.

Another object of this invention is to provide novel N-alkenyl amine-N-oxide compounds.

DETAILED DISCLOSURE

The compounds of this invention possess excellent and surprisingly superior properties compared to the closest compounds of the prior art in several important facets. These are:

(1) they exhibit superior polymer stabilization properties during the processing of polymers at elevated temperatures;

(2) they provide resistance to color development during processing especially when used in conjunction with a phenolic antioxidant;

(3) they are less prone to oxidation by ambient air during storage or in handling;

(4) they do not interact with polymerization catalysts such as the sulfonic acid catalysts used during the curing of aminoplast resin systems;

(5) they are more soluble in typical organic solvents and are more compatible with the polymeric substrates being stabilized;

(6) they resist moisture pickup and provide low water carry-over properties; and (7) they inhibit sludge formation in and control viscosity increase of motor oil formulations during use.

The instant invention pertains to stabilized compositions which comprise (a) an organic material subject to oxidative, thermal or actinic induced degradation, and (b) an effective stabilizing amount of a compound of formula I

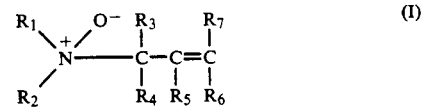

wherein $R_1$ and $R_2$ are independently hydrogen, a straight or branched chain alkyl of 1 to 36 carbon atoms, alkyl of 1 to 18 carbon atoms terminated by a group $-OR_8$, $-NR_9R_{10}$, $-SR_{11}$, $-COOR_{12}$ or $-CONR_{13}R_{14}$ or interrupted by arylene of 6 to 10 carbon atoms, $-O-$, $-S-$, $-SO-$, $-SO_2-$, $-COO-$, $-OCO-$, $-CONR_{15}-$, $-NR_{15}CO-$ or $-NR_{16}$ where $R_8$, $R_9$, $R_{10}$, $R_{11}$, $R_{12}$, $R_{13}$, $R_{14}$, $R_{15}$ and $R_{16}$ are independently hydrogen, alkyl of 1 to 18 carbon atoms or alkenyl of 3 to 6 carbon atoms; or $R_1$ and $R_2$ are independently cycloalkyl of 5 to 12 carbon atoms, phenylalkyl of 7 to 15 carbon atoms, said phenylalkyl substituted on the phenyl ring by alkyl of 1 to 12 carbon atoms or by α-cumyl; aryl of 6 to 14 carbon atoms, said aryl substituted by one or two alkyl of 1 to 24 carbon atoms, $R_3$ and $R_4$ are independently hydrogen, alkyl of 1 to 9 carbon atoms, said alkyl substituted by $-OH$ or by acetoxy; alkenyl of 3 to 6 carbon atoms or aryl of 6 to 10 carbon atoms, and $R_5$, $R_6$ and $R_7$ are independently hydrogen, alkyl of 1 to 9 carbon atoms, said alkyl substituted by $-OH$ or by acetoxy; alkenyl of 3 to 6 carbon atoms, aryl of 6 to 10 carbon atoms or a group of formula II

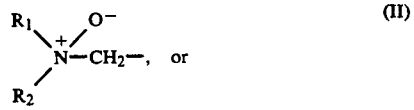

$R_3$ and $R_4$, or $R_3$ and $R_5$, or $R_3$ and $R_7$, or $R_4$ and $R_5$, or $R_4$ and $R_7$, or $R_5$ and $R_6$, or $R_6$ and $R_7$ together are straight or branched chain alkylene of 2 to 8 carbon atoms to form a cycloalkyl or cycloalkenyl ring with 5 or 6 ring atoms.

Preferably the instant compounds of formula I are those where

R$_1$ and R$_2$ are independently straight or branched chain alkyl of 1 to 20 carbon atoms, alkyl of 1 to 18 carbon atoms terminated by a group —OR$_8$, —NR$_9$R$_{10}$, —SR$_{11}$, —COOR$_{12}$ or —CONR$_{13}$R$_{14}$ or interrupted by phenylene, —O—, —S—, —SO—, —SO$_2$—, —COO—, —OCO—, —CONR$_{15}$—, —NR$_{15}$CO— or —NR$_{16}$—, where R$_8$, R$_9$, R$_{10}$, R$_{11}$, R$_{12}$, R$_{13}$, R$_{14}$, R$_{15}$ and R$_{16}$ are independently hydrogen or alkyl of 1 to 18 carbon atoms; or R$_1$ and R$_2$ are independently cycloalkyl of 5 to 7 carbon atoms, benzyl, benzyl substituted on the phenyl ring by alkyl of 1 to 12 carbon atoms or by α-cumyl; aryl of 6 to 14 carbon atoms or said aryl substituted by one or two alkyl of 1 to 24 carbon atoms, R$_3$ is hydrogen or alkyl of 1 to 4 carbon atoms, R$_4$ is hydrogen, alkyl of 1 to 4 carbon atoms or phenyl, R$_5$ and R$_6$ are independently hydrogen, alkyl of 1 to 9 carbon atoms or a group of formula II, and R$_7$ is hydrogen, alkyl of 1 to 9 carbon atoms or phenyl.

Most preferably the instant compounds of formula I are those where

R$_1$ and R$_2$ are independently alkyl of 8 to 18 carbon atoms, cyclohexyl, benzyl, phenyl, 1-naphthyl, or said phenyl or said naphthyl substituted by one or two alkyl of 4 to 12 carbon atoms, R$_3$ is hydrogen, R$_4$ is hydrogen or methyl, R$_5$ and R$_6$ are independently hydrogen or a group of formula II, and R$_7$ is hydrogen.

When any of the aforementioned groups are alkyl, they are, for example, methyl, ethyl, isopropyl, n-butyl, sec-butyl, tert-butyl, isoamyl, tert-amyl, n-hexyl, 2-ethylhexyl, isooctyl, n-octyl, nonyl decyl, undecyl, lauryl, tridecyl, tetradecyl, hexadecyl, heptadecyl, octadecyl, eicosyl, tricontyl and branched isomers thereof.

Cycloalkyl of 5 to 12 carbon atoms includes, for example, cyclopentyl, cyclohexyl, cycloheptyl, cyclooctyl and cyclododecyl.

Phenylalkyl of 7 to 15 carbon atoms includes, for example, benzyl, phenethyl, α-methylbenzyl and β-methylphenethyl.

Aryl of 6 to 14 carbon atoms includes, for example, phenyl, 1-naphthyl, 2-naphthyl, xenyl, anthracyl and phenanthryl.

Aryl substituted by alkyl is, for example, tolyl, xylyl, mesityl, ethylphenyl, tert-butylphenyl, tert-octylphenyl, tert-dodecylphenyl, tert-butylnaphthyl or tert-octylnaphthyl.

The starting materials from making the instant compounds of formula I are largely items of commerce and can be made by known methods.

The instant compounds of formula I are conveniently prepared the allylation of a secondary amine using an alkenyl (allyl) halide by the method taught by A. W. Weston et al, J. Am. Chem. Soc., 65, 674 (1943) followed by oxidation of the N-alkenyl(allyl) tertiary amine to the corresponding N-alkenyl(allyl) amine-N-oxide.

A preferred embodiment of the instant compounds is derived from hydrogenated tallow amine which is a mixture of secondary amines of the general formula

T$_1$T$_2$NH where the typical distribution of the alkyl substituents is as follows:

| T$_1$ | T$_2$ | % |
|---|---|---|
| C$_{16}$ | C$_{14}$ | 1.9 |
| C$_{16}$ | C$_{16}$ | 12.4 |
| C$_{16}$ | C$_{17}$ | 2.8 |
| C$_{16}$ | C$_{18}$ | 36.0 |
| C$_{17}$ | C$_{18}$ | 3.9 |
| C$_{18}$ | C$_{18}$ | 39.0 |
| other | | 4.0 |

It is clear that the di(hydrogenated tallow)amine originating from animal sources may well vary somewhat in the specific distribution of the alkyl substituents, but the di(hydrogenated tallow)amine contains major amounts of N,N-dihexadecylamine, N,N-dioctadecylamine and N-hexadecyl-N-octadecylamine. The individual components of the mixture can be separated by distillation under high vacuum.

However, for the purposes of this invention, there is no need to carry out such a separation and the hydroxylamine prepared from the di(hydrogenated tallow)amine represents a preferred starting material for making the N-alkenyl compounds of this invention.

The compositions where component (a) is a synthetic polymer are especially part of this invention, most particularly when the synthetic polymer is a polyolefin such as polypropylene.

The instant compounds are effective stabilizers for organic materials or compositions of matter comprising organic matter in that they reduce degradation resulting from long term oxidative and/or thermal aging and effectively protect said materials from actinic radiation.

In addition, the instant compounds show little tendency to evaporate or sublime from the organic compositions during thermal processing. Thus, the instant compounds are effective process stabilizers for organic polymers processed at elevated temperatures.

In still another end-use application, the instant compounds of formula I, especially those where R$_1$ and R$_2$ are aryl, are useful in stabilizing, by inhibiting oxidation, industrial lubricants such as lubricating oils, turbine oils, transformer oils, transmission fluids, glass-annealing oils, greases, steam turbine oils, gasoline engine oils, diesel engine oils, jet engine oils, metal working fluids and the like. They are also effective in stabilizing waxes, heating oil, bunker and residual oils, asphalt, gasoline and jet engine fuel.

Still another aspect of the instant invention are the novel compounds of formula I

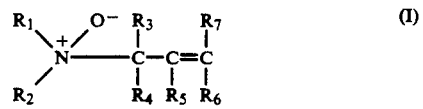

wherein

R$_1$ and R$_2$ are independently alkyl of 8 to 36 carbon atoms, benzyl, benzyl substituted on the phenyl ring by alkyl of 1 to 18 carbon atoms or by α-cumyl, aryl of 6 to 14 carbon atoms or said aryl substituted by one or two alkyl of 1 to 24 carbon atoms, R$_3$ and R$_4$ are independently hydrogen, alkyl of 1 to 9 carbon atoms, alkenyl of 3 to 6 carbon atoms or aryl of 6 to 10 carbon atoms, and R$_5$, R$_6$ and R$_7$ are independently hydrogen, alkyl of 1 to 9 carbon atoms, alkenyl of 3 to 6 carbon atoms, aryl of 6 to 10 carbon atoms or a group of formula II

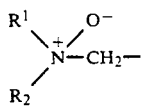
(II)

The most preferred novel compounds of the instant invention are those where $R_1$ and $R_2$ are independently alkyl of 8 to 18 carbon atoms, benzyl, phenyl, 1-naphthyl, or said phenyl or said naphthyl substituted by one or two alkyl of 4 to 12 carbon atoms, $R_3$ is hydrogen, $R_4$ is hydrogen or methyl, $R_5$ and $R_6$ are independently hydrogen or a group of formula II, and $R_7$ is hydrogen.

The most preferred novel compounds of this invention are those where $R_1$ and $R_2$ are independently alkyl of 12 to 18 carbon atoms, benzyl, phenyl, 1-naphthyl or said phenyl or said naphthyl substituted by one or two alkyl of 4 to 8 carbon atoms, $R_3$ is hydrogen, $R_4$ is hydrogen, $R_5$ is hydrogen or a group of formula II, $R_6$ is hydrogen or a group of formula II, and $R_7$ is hydrogen.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/ ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonyl-phenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.
1.5. Benzyl compounds, for example, 1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate

| 1.7. Esters of β-(3,5-di-tert-butyl-4-hydroxyphenyl)-propionic acid with monohydric or polyhydric alcohols, for example, | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

| 1.8. Esters of β-(5-tert-butyl-4-hydroxy-3-methylphenyl)-propionic acid with monohydric or polyhydric alcohols, for example, | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example,
diphenylamine, N-phenyl-1-naphthylamine, N-(4-tert-octylphenyl)-1-naphthylamine,
4,4'-di-tert-octyl-diphenylamine, reaction product of N-phenylbenzylamine and
2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyano-vinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris(2,2,6,6-tetramethylpiperidyl)-nitrilotriacetate, tetrakis-(2,2,6,6-tetramethyl-4-piperidyl)-1,2,3,4-butanetetra-carbonic acid, 1,1'(1,2-ethanediyl)-bis-(3,3,5,5-tetramethylpiperazinone, bis(1-octyloxy-2,2,6,6-tetramethylpiperidin-4-yl) sebacate.

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alphaheptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The following examples are presented for the purpose of illustration only and are not to be construed to limit the nature or scope of the instant invention in any manner whatsoever.

EXAMPLE 1

N-Allyl-N,N-dioctadecylamine-N-oxide

Into a cooled solution of 5.0 g (9 mmol) of N-allyl-N,N-dioctadecylamine in 50 ml of chloroform at 0° C. under a nitrogen atmosphere is added dropwise with stirring a solution of 2.82 g (9 mmol) of 55% active m-chloroperbenzoic acid in 25 ml of chloroform. After the addition is complete (approximately 10 minutes), the resultant solution is allowed to warm to ambient temperature (about 22°–24° C.). The reaction is complete after about 2 hours when TLC analysis (silica gel, 19:1 v/v ethyl acetate:methanol) indicates the starting material has completely reacted. The reaction mixture is passed through a short column of basic alumina using chloroform as an eluent to give 5.2 g (quantitative yield) of the title compound as a white solid melting at 59°–64° C.

TLC and $^1$HNMR analyses confirm the structure of the title compound.

EXAMPLE 2

N-Allyl-N,N-bis(hydrogenated tallow)amine-N-oxide

Following the general procedure of Example 1 and using an equivalent amount of N-allyl-N,N-bis(hydrogenated tallow)amine in place of N-allyl-N,N-dioctadecylamine the title compound is prepared.

EXAMPLE 3

N-Allyl-N,N-dibenzylamine-N-oxide

Following the general procedure of Example 1, the title compound is prepared starting with N-allyl-N,N-dibenzylamine as starting material.

EXAMPLE 4

N-Allyl-N,N-dioctylamine-N-oxide

The title compound is prepared following the general procedure of Example 1 starting from N-allyl-N,N-dioctylamine.

EXAMPLE 5

N-Allyl-N,N-diphenylamine-N-oxide

The title compound is prepared starting with N-allyl-N-N-diphenylamine using the general procedure of Example 1.

EXAMPLE 6

N,N'-But-2-en-1,4-diyl-bis(N,N-dibenzylamine)-N,N'-dioxide

The title compound is prepared following the general procedure of Example 1 starting with N,N'-but-2-en-1,4-diyl-bis(N,N-dibenzylamine).

EXAMPLE 7

N,N'-But-2-en-1,4-diyl-bis(N,N-diphenylamine)-N,N'-dioxide

The title compound is prepared following the general procedure of Example starting with N,N'-but-2-en-1,4-diyl-bis(N,N-diphenylamine).

EXAMPLE 8

Process Stabilization of Polypropylene at 280° C.

The test stabilizers are solvent blended using methylene chloride into unstabilized polypropylene (PRO- FAX 6501 Himont) which already contains 0.1% by weight of calcium stearate. After removal of solvent by evaporation under reduced pressure, the resin is extruded using an MPM one-inch single screw extruder under the following extruder conditions:

| Screw RPM | 80 |
|---|---|
| Cylinder #1 heater zone | 243° C. |
| Cylinder #2 heater zone | 268° C. |
| Cylinder #3 heater zone | 279° C. |
| Gate, adapter die | 282° C. |
| Melt Temperature | 280–283° C. |
| Residence Time seconds | 45 |

After the first and fifth extrusions, the melt flow rate (MFR) is determined by the ASTM method 1238 condition L. The MFR with polypropylene varies inversely with molecular weight. The higher is the MFR, the lower is the molecular weight. A relative change in MFR between the first and fifth extrusion values indicates that the relative effectiveness of the test stabilizer in protecting the polypropylene from degradation during processing at the elevated temperature. The MFR data for a number of test stabilizers are given in the table below.

| Additive* Compound of | Additive Concentration (% by weight) | MFR (g/10 min) After Extrusion 1 | 5 |
|---|---|---|---|
| AO A | 0.1 | 17.9 | 25.6 |
| AO A plus Example 1 | 0.1 0.05 | 8.6 | 12.5 |

*AO A is neopentanetetrayl tetrakis(3,5-di-tert-butyl-4-hydroxyhydrocinnamate).
**Base resin contains 0.1% by weight of calcium stearate.

The instant N-allyl N-oxide compound provides good process stabilization to polypropylene.

EXAMPLE 9

Color Stabilization of Polypropylene

This example illustrates the color stabilizing effectiveness of the instant compounds in combination with a phenolic antioxidant.

When pellets obtained after the fifth extrusion as described in Example 8 are compression molded into 125 mil (3.2 mm) thick plaques at 193° C., the yellowness index (YI) values on said plaques are determined according to ASTM test method D1925. The results are given below.

| Additive* Compound of | Additive Concentration (% by weight) | Yellowness Index |
|---|---|---|
| AO A | 0.1 | 17.7 |
| AO A plus Example 1 | 0.1 0.05 | 13.5 |

The plaque containing both the instant compound and the phenolic antioxidant develops far less color than the plaque with the phenolic antioxidant alone.

EXAMPLE 10

Standard Test Method for Oxidation Stability of Gasoline Automotive Engine Oils by Thin-Film Oxygen Uptake (TFOUT)

The antioxidant effectiveness of the instant stabilizers in engine oils is evaluated by the ASTM test method, D4742. A 1.5 gram test sample of 10W-30 engine oil, formulated to meet SD/CC quality level containing 0.5% by weight of the test compound is placed in the test apparatus. The test is then completed according to the standard method procedure and the oxidation induction time, in minutes, is recorded. A longer induction time indicates greater oxidation stability. The compound of Example 5 is an effective antioxidant for engine oils.

EXAMPLE 11

When using the test procedure of Example 10 the N-alkenyl N-oxide compound of Example 5 is replaced by the instant compound of Example 7, the compound of Example 7 is also shown to be an effective antioxidant for engine oils.

What is claimed is:
1. A stabilized composition which comprises
   (a) a synthetic polymer subject to oxidative, thermal or actinic-induced degradation, and
   (b) an effective stabilizing amount of a compound of formula I

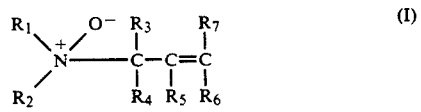

wherein
$R_1$ and $R_2$ are independently hydrogen, a straight or branched chain alkyl of 1 to 36 carbon atoms, or $R_1$ and $R_2$ are independently cycloalkyl of 5 to 12 carbon atoms, phenylalkyl of 7 to 15 carbon atoms, said phenylalkyl substituted on the phenyl ring by alkyl of 1 to 18 carbon atoms or by α-cumyl; carbocyclic aryl of 6 to 14 carbon atoms or said aryl substituted by one or two alkyl of 1 to 24 carbon atoms,
$R_3$ and $R_4$ are independently hydrogen, alkyl of 1 to 9 carbon atoms, alkenyl of 3 to 6 carbon atoms or carbocyclic aryl of 6 to 10 carbon atoms, and
$R_5$, $R_6$ and $R_7$ are independently hydrogen, alkyl of 1 to 9 carbon atoms, alkenyl of 3 to 6 carbon atoms, carbocyclic aryl of 6 to 10 carbon atoms, or a group of formula II

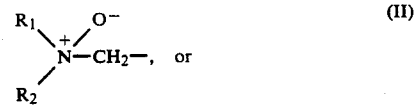

$R_3$ and $R_4$, or $R_3$ and $R_5$, or $R_3$ and $R_7$, or $R_4$ and $R_5$, or $R_4$ and $R_7$, or $R_5$ and $R_6$, or $R_6$ and $R_7$ together are a straight or branched chain alkylene of 2 to 8 carbon atoms to form a cycloalkyl or cycloalkenyl ring with 5 or 6 ring atoms.
2. A composition according to claim 1 wherein the synthetic polymer is a polyolefin.
3. A composition according to claim 2 wherein the polyolefin is polypropylene.
4. A composition according to claim 1 wherein the compound of formula I,
   $R_1$ and $R_2$ are independently a straight or branched chain alkyl of 1 to 20 carbon atoms, or $R_1$ and $R_2$ are cycloalkyl of 5 to 7 carbon atoms, benzyl, benzyl substituted on the phenyl ring by alkyl of 1 to 12 carbon atoms or by α-cumyl, carbocyclic aryl of 6 to 14 carbon atoms or said aryl substituted by one or two alkyl of 1 to 24 carbon atoms,
$R_3$ is hydrogen or alkyl of 1 to 4 carbon atoms,
$R_4$ is hydrogen, alkyl of 1 to 4 carbon atoms or phenyl,
$R_5$ and $R_6$ are independently hydrogen, alkyl of 1 to 9 carbon atoms, or a group of formula II, and
$R_7$ is hydrogen, alkyl of 1 to 9 carbon atoms or phenyl.

5. A composition according to claim 4 wherein $R_1$ and $R_2$ are independently alkyl of 8 to 18 carbon atoms, cyclohexyl, benzyl, phenyl, 1-naphthyl or said phenyl or said naphthyl substituted by one or two alkyl of 4 to 12 carbon atoms,
$R_3$ is hydrogen,
$R_4$ is hydrogen or methyl,
$R_5$ and $R_6$ are independently hydrogen or a group of formula II, and
$R_7$ is hydrogen.

6. A composition according to claim 1 wherein component (b) is N-allyl-N,N-dioctadecylamine-N-oxide.

* * * * *